United States Patent [19]
Suzuki

[11] Patent Number: 5,876,355
[45] Date of Patent: Mar. 2, 1999

[54] HOLDER FOR VACUUM BLOOD COLLECTING CONTAINER

[76] Inventor: Ryuji Suzuki, 3-6-1003, Nishikasai 6-chome, Edogawa-ku, Tokyo, Japan

[21] Appl. No.: 800,982

[22] Filed: Feb. 19, 1997

[51] Int. Cl.$^6$ ........................................................ A61B 5/00
[52] U.S. Cl. .............................................................. 600/576
[58] Field of Search .................................... 600/576–579, 600/583

[56] References Cited

U.S. PATENT DOCUMENTS

| | | | |
|---|---|---|---|
| 4,409,990 | 10/1983 | Mileikowsky | 600/576 |
| 4,942,881 | 7/1990 | Al-Soufi et al. | 600/576 |
| 5,117,837 | 6/1992 | Wanamaker et al. | 600/576 |

*Primary Examiner*—Max Hindenburg
*Attorney, Agent, or Firm*—Abelman, Frayne & Schwab

[57] ABSTRACT

A holder for a vacuum blood collecting container in which commercially available blood collecting needles can be engaged and disengaged easily and certainly, a pair of needle mounting and supporting members are arranged to be displaced relatively to have a mutual engaging position where the blood collecting needle is retained and a separated position where the blood collecting needle is released.

4 Claims, 2 Drawing Sheets

HOLDER FOR VACUUM BLOOD COLLECTING CONTAINER

BACKGROUND OF THE INVENTION

1. Field of the Invention

The present invention relates to a holder for a vacuum blood collecting container, having a needle mounting portion provided at its one end for supporting a blood collecting needle and a portion at the other end for receiving a vacuum blood collecting container when a blood collection is carried out.

2. Prior Art

Conventionally, various types of holders are known as such kind of vacuum blood correcting container holder. Generally, a conventional holder has one end portion which is integrally formed with a needle mounting and supporting portion. The needle mounting and supporting portion engages with a male screw disposed in the outer periphery of a hub mounted in the intermediary section of a blood collecting needle, one end of which pierces through the vein of the blood examinee and the other end is inserted into the blood collecting container. (For example, refer to Japanese Patent Publication No. 7-32766).

According to such kind of vacuum blood collecting container holder, a blood collecting needle to be used is screw engaged with the needle mounting and supporting portion provided at one end of the holder, and after blood collection the blood collecting needle is rotated to be disengaged from the holder so as to be disposed of, while the vacuum blood collecting container holder is ready to be used for subsequent blood collection. Thus, to secure prevention of infection or contagion and safety, the blood collecting needle is disposed of after use, but the holder is repeatedly used.

In such screw engaging type of vacuum blood collecting holders any specific problem does not occur even if the blood collector directly touches the blood collecting needle since the needle is used for the first time when it is mounted. However, when the needle is disengaged after blood collection, not only there arises a risk for the blood collector of touching the needle adhered with blood but also it is necessary to rotate the blood collecting needle to disengage from screwing thereby taking specific time and work for operation. On the other hand, since the blood collecting needle employed under vacuum system is mounted normally with a cap the engagement and disengagement of the blood collecting needle with and from the holder must be effected in the state where the cap is mounted. Such kind of blood collecting container holder is excellent from the viewpoint of safety when mounting, but unless re-capped after blood collection it may be impossible or hard to separate the needle, so that it needs a specific work for the engaging and disengaging operation.

By the way, what is required for such kind of blood collecting equipment is to previously prevent infection or contagion caused by accidental pricking of the blood collecting needle, which pricking may occur in blood collecting or examining work whereby human and economic loss are reduced. However, as mentioned above, in known blood collecting devices it takes time and requires specific labor to engage or disengage the blood collecting needle, and further a danger of accidental pricking of the needle to the needle operator is involved there thereby requiring an improvement.

It is, therefore, an object of the present invention to provide a holder for a vacuum blood collecting container in which it is possible to easily remove, after blood collection by vacuum blood collecting tubes or containers, the blood collecting needle from the holder, it is capable of mounting and supporting the blood collecting needle steadily and safely, and the manufacturing cost is low.

Another object of the present invention is to provide a holder for a vacuum blood collecting container in which known blood collecting needles are usable as they are.

SUMMARY OF THE INVENTION

According to one aspect of the present invention there is provided a holder for a vacuum blood collecting container including a hollow holder body for receiving a vacuum blood collecting tube or container, the holder body having one end on which a needle mounting and supporting means is provided for mounting and supporting a blood collecting needle and the other end opended from which the vacuum blood collecting tube or container can be inserted, wherein said needle mounting and supporting means comprises a pair of needle mounting and supporting members each of which has an inner peripheral surface semi-annular in section and a female screw halve provided on the inner peripheral surface and intended to engage with a male screw provided in a hub of the blood collecting needle, and the the needle mounting and supporting members are arranged to be displaced relatively to have a mutual engaging position where the blood collecting needle is retained and a separated position where the blood collecting needle is released.

In the holder according to one aspect of the present invention, one of the paired needle mounting and supporting members is fixed coaxially with the holder body at the surface on one end of said holder body, and the other of said members is mounted slidably laterally to the fixed member so that the two needle mounting and supporting members can be retained in their engaging position.

According to another aspect of the present invention, there is provided a holder for a vacuum blood collecting container including a hollow holder body for receiving a vacuum blood collecting tube or container, the holder body having one end on which a needle mounting and supporting means is provided for mounting and supporting a blood collecting needle and the other end opended from which the vacuum blood collecting tube or container can be inserted, wherein said needle mounting and supporting means comprises a pair of needle mounting and supporting members each of which has an inner peripheral surface semi-annular in section and a female screw halve provided on the inner peripheral surface and intended to engage with a male screw provided in a hub of the blood collecting needle, the the needle mounting and supporting members are arranged to be displaced relatively to have a mutual engaging position where the blood collecting needle is retained and a separated position where the blood collecting needle is released, and a stopper member is provided for retaining said pair of needle mounting and supporting members in their mutually engaged position.

Preferably, the stopper member may be mounted in the outer peripheral surface adjacent to one end of the holder body, and it engages with the movable needle mounting and supporting member so as to be retained in their engaged position.

In the holder for the vacuum blood collecting container thus constructed in the present invention, at least one of the two needle mounting and supporting members is capable of laterally sliding between the mutually engaging position of the two members and their separated position, said members have inner peripheral surfaces approximately semi-annular in section which are provided with the female screw halves engaging with the male screw disposed in the hub of the blood collecting needle, and therefore, it is possible to easily mount or remove a screw-in type blood collecting needle, with one touch and safely without touching the blood collecting needle itself.

DESCRIPTION OF PREFERRED EMBODIMENTS

The invention will now be described more in detail, by way of example, with reference to the accompanying drawings.

Figure 1:
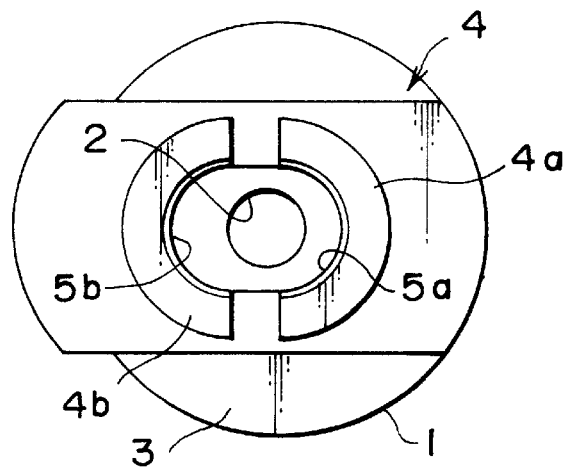
FIG. 1 is a plan view showing, in the opened or separated state, the essential parts in the holder according to an embodiment of the invention.
Figure 2:
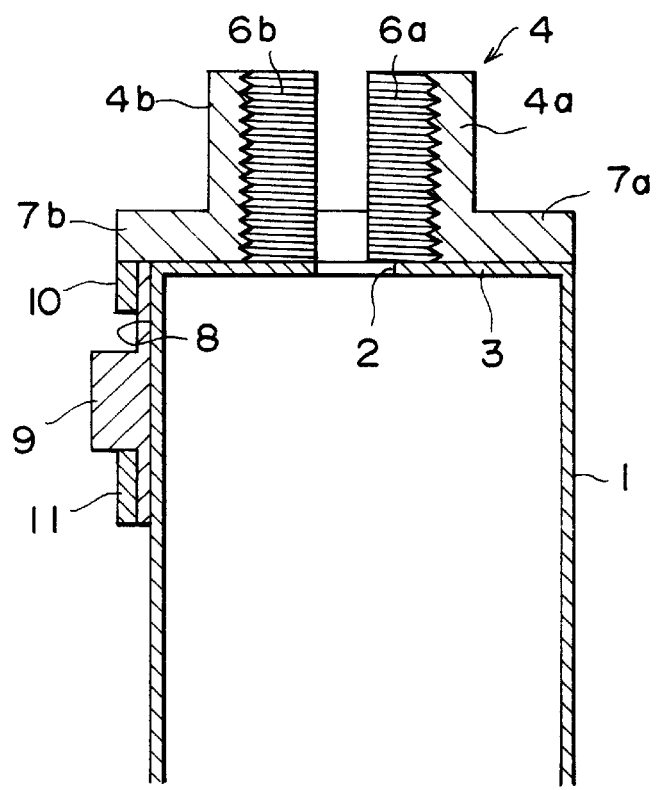
FIG. 2 is a vertical section of the holder of FIG. 1.
Figure 3:
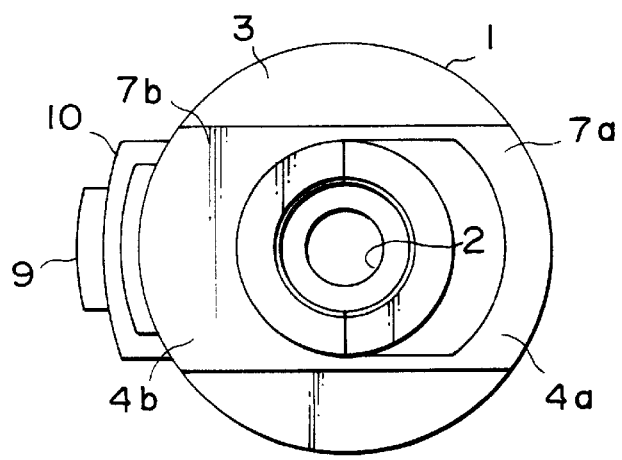
FIG. 3 is a plan view where the holder of FIG. 1 is shown in a closed or engaged state.
Figure 4:
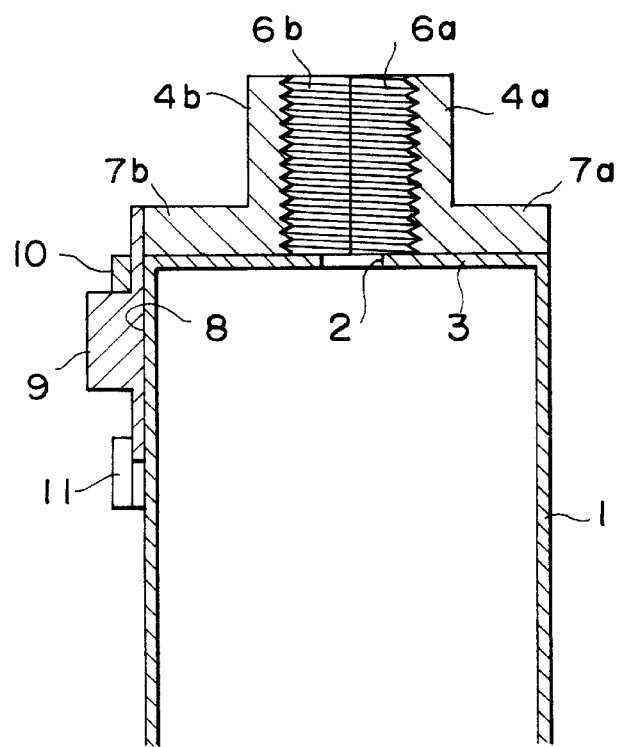
FIG. 4 is a vertical section of the holder in the state of FIG. 3.

In the embodiment shown in FIGS. 1 to 4, the reference numeral 1 designates a hollow holder body made of a suitable synthetic resinous material. The holder body 1 is provided with an opening 2 on an end wall 3 for passing a blood collecting needle not shown. A needle mounting and supporting device 4 is provided upon the outer surface of the end wall 3, and comprises a pair of needle mounting and supporting members 4a and 4b made of a suitable synthetic resinous material. The respective needle mounting and supporting members 4a and 4b have inner peripheral surfaces 5a and 5b approximately semi-annular in section, respectively, on which female screw halves 6a and 6b are formed. The female screw halves 6a and 6b are designed to be engaged with a male screw (not shown) arranged in the hub of the blood collecting needle. Also, the respective needle mounting and supporting members 4a and 4b include base portions 7a and 7b which are mounted onto the outer surface of the end wall 3. The member 4a, one of the two needle mounting and supporting members 4a and 4b, is secured coaxially with the holder body 1 to the outer surface of the end wall 3 of the holder body while the other member 4b is mounted laterally slidably relative to said one member 4a. Thus, said pair of these needle mounting and supporting members 4a and 4b are constructed to take both the mutually engaging position illustrated in FIGS. 3 and 4 and mutually separated positions illustrated in FIGS. 1 and 2.

Further, on an external peripheral surface 8 adjacent to one end of the holder body 1 is provided a stopper member 9 which is intended to retain said pair of the needle mounting and supporting members 4a and 4b in their mutually engaging position. The stopper member 9 is supported, as shown, slidably along the longitudinal direction of the external peripheral surface 8 of the holder body 1 by means of two band-like supporting members 10 and 11 secured integrally with the external peripheral surface 8 of the holder body 1. That is, the stopper member 9 is released from the engagement with the other needle mounting and supporting member 4b in the storing position shown in FIGS. 1 and 2 so as not to hinder said member 4b from its lateral movement. On the other hand, in the projecting position shown in FIGS. 3 and 4, the stopper member 9 is adapted such that its upper end abuts against the base portion 7b of the other needle mounting and supporting member 4b. With such arrangement, said pair of the needle mounting and supporting members 4a and 4b are held in their mutually engaging position to allow the blood collecting needle to be securely mounted and supported.

In the operation of the holder thus constituted and illustrated in the drawings, the other needle mounting and supporting member 4b is slided toward the one needle mounting and supporting member 4a so as to be met together, and in that state the stopper member 9 is slided upward whereby said members 4a and 4b in pair are retained in their engaged position. In that state the blood collecting needle is screwed-in for securing. After the blood collecting operation the needle mounding and supporting device 4 is directed downward and the stopper member 9 is slided for retraction whereby the other needle mounting and supporting member 4b is released from its hooking while moving in the direction of going away from the one needle mounting and supporting member 4a, when the blood collecting needle is released from its screwing engagement to be dropped down. Additionally, though not shown in the drawings, by incorporating a coil spring that is forced toward the opening direction into the other needle mounting and supporting member 4b thereby always to force the other needle mounting supporting member 4b toward the direction withdrawing away from the one needle mounting and supporting member 4a, it is capable of disengaging the blood collecting needle more easily by the releasing operation of the stopper member 9.

In the embodiment illustrated in the drawings either of a pair of needle mounting and supporting members is fixed whereas the other is made movable. Alternatively, it is possible as necessary that both of the two members are movable and each of them is incorporated with a stopper member. It is also possible to adopt, for example, a suitable snapping stopper mechanism instead of the stopper member.

Moreover, a relative screw or a non-relative modified screw may be substituted for the female screw provided in the needle mounting and supporting members.

As described above in detail, according to the present invention, since at least one of the needle mounting and supporting members is adapted to be slidable laterally so that said pair of the needle mounting and supporting members have the mutually engaging position and the separated position, the blood collecting needle set in screwing-in system can be easily disengaged thereby enabling the blood collecting needle to be mounted safely and released with one touch without being touched. As a result, the blood collecting needle need not be removed being re-capped after blood collection whereby the needle can be easily disposed of while preventing an erroneous pricking of the needle. This extensively contributes infection prevention and the control of time and cost relative thereto.

I claim:

1. A holder for a vacuum blood collecting container including a hollow holder body for receiving a vacuum blood collecting tube or container, the holder body having one end closed by a wall on which a needle mounting and supporting means is provided for mounting and supporting a blood collecting needle and a second end which is open and in which the vacuum blood collecting tube or container can be inserted, wherein said needle mounting and supporting means comprises a pair of needle mounting and supporting members each of which has an inner peripheral surface semi-annular in section and a female screw half provided on the inner peripheral surface and intended to engage with a male screw provided in a hub of the blood collecting needle, and the needle mounting and supporting members are arranged on an outer surface of the end wall of the holder body so that at least one of the needle mounting and supporting members is adapted to slide on the outer surface of the end wall of the holder body so as to have a mutual engaging position where the blood collecting needle is retained and a separated position where the blood collecting needle is released.

2. A holder as set forth in in claim 1, wherein one of the paired needle mounting and supporting members is fixed coaxially with the holder body at the surface on one end of said holder body, and the other of said members is mounted slidably laterally to the fixed member so that the two needle mounting and supporting members can be retained in their engaging position.

3. A holder for a vacuum blood collecting container including a hollow holder body for receiving a vacuum blood collecting tube or container, the holder body having one end closed by a wall on which a needle mounting and supporting means is provided for mounting and supporting a blood collecting needle and a second end which is open and in which the vacuum blood collecting tube or container can be inserted, wherein said needle mounting and supporting means comprises a pair of needle mounting and supporting members each of which has an inner peripheral surface semi-annular in section and a female screw half provided on the inner peripheral surface and intended to engage with a male screw provided in a hub of the blood collecting needle, and the needle mounting and supporting members are arranged on an outer surface of the end wall of the holder body so that at least one of the needle mounting and supporting members is adapted to slide on the outer surface of the end wall of the holder body so as to have a mutual engaging position where the blood collecting needle is retained and a separated position where the blood collecting needle is released, and a stopper member is provided for retaining said pair of needle mounting and supporting members in their mutually engaged position.

4. A holder as set forth in in claim 3, wherein the stopper member is mounted in the outer peripheral surface adjacent to one end of the holder body, and it engages with the movable needle mounting and supporting member so as to be retained in their engaged position.

* * * * *